United States Patent
Tatsuda

(10) Patent No.: US 10,341,523 B2
(45) Date of Patent: Jul. 2, 2019

(54) PRINTER AND CONTROL METHOD OF A PRINTER

(71) Applicant: SEIKO EPSON CORPORATION, Tokyo (JP)

(72) Inventor: Tetsuo Tatsuda, Ina (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 15/975,431

(22) Filed: May 9, 2018

(65) Prior Publication Data

US 2018/0332189 A1 Nov. 15, 2018

(30) Foreign Application Priority Data

May 10, 2017 (JP) .................. 2017-093695

(51) Int. Cl.
| | | |
|---|---|---|
| *H04N 1/23* | (2006.01) | |
| *B41J 2/15* | (2006.01) | |
| *B41J 25/00* | (2006.01) | |
| *B41J 25/308* | (2006.01) | |
| *B41J 25/316* | (2006.01) | |
| *G01N 21/00* | (2006.01) | |
| *H04N 5/225* | (2006.01) | |
| *B41J 2/01* | (2006.01) | |
| *B41J 19/18* | (2006.01) | |
| *B41J 29/38* | (2006.01) | |

(52) U.S. Cl.
CPC ............... *H04N 1/23* (2013.01); *B41J 2/01* (2013.01); *B41J 2/15* (2013.01); *B41J 19/18* (2013.01); *B41J 25/001* (2013.01); *B41J 25/003* (2013.01); *B41J 25/3086* (2013.01); *B41J 25/316* (2013.01); *B41J 29/38* (2013.01); *G01N 21/00* (2013.01); *H04N 5/2257* (2013.01)

(58) Field of Classification Search
CPC ....... B41J 2/01; B41J 2/15; B41J 19/18; B41J 25/001; B41J 25/003; B41J 25/3086; B41J 25/316; B41J 29/38
See application file for complete search history.

(56) References Cited

U.S. PATENT DOCUMENTS

| 8,169,657 B2 | 5/2012 | Wang et al. |
| 9,908,323 B2 | 3/2018 | Rossell et al. |

(Continued)

FOREIGN PATENT DOCUMENTS

| JP | 2005-053228 A | 3/2005 |
| JP | 2007-185870 A | 7/2007 |

(Continued)

OTHER PUBLICATIONS

Extended European Search Report dated Oct. 5, 2018 in related European Appl. 18171617.6 (7 pgs.).

(Continued)

*Primary Examiner* — Lamson D Nguyen
(74) *Attorney, Agent, or Firm* — Foley & Lardner LLP

(57) ABSTRACT

Provided is a printer having: a carriage configured to carry and move a printhead; a camera attached to the carriage and configured to photograph an image printed by the printhead; an adjustment mechanism configured to adjust an installation position of the camera; and a processor configured to control to move the carriage to a position of a predetermined specific mark, photograph the specific mark by the camera, and based on a photographed image of the specific mark, adjust an installation position of the camera by the adjustment mechanism.

10 Claims, 5 Drawing Sheets

(56) References Cited

U.S. PATENT DOCUMENTS

| | | | |
|---|---|---|---|
| 2005/0024410 A1 | 2/2005 | Subirada et al. |
| 2010/0121477 A1 | 5/2010 | Jonas et al. |
| 2011/0273502 A1 | 11/2011 | Eun et al. |
| 2012/0147074 A1 | 6/2012 | Ikeda et al. |
| 2014/0259595 A1 | 9/2014 | Von Essen et al. |

FOREIGN PATENT DOCUMENTS

| | | |
|---|---|---|
| JP | 2009-066902 A | 4/2009 |
| JP | 2010-030257 A | 2/2010 |
| JP | 2018-187873 A | 11/2018 |
| JP | 2018-187874 A | 11/2018 |

OTHER PUBLICATIONS

Non-Final Office Action dated Jan. 11, 2019 in related U.S. Appl. No. 15/974,265 (7 pgs.).

PRINTER AND CONTROL METHOD OF A PRINTER

This application claims priority under 35 U.S.C. § 119 to Japanese Patent Application No. 2017-93695 filed on May 10, 2017, the entire disclosure of which is expressly incorporated by reference herein.

BACKGROUND

1. Technical Field

The present invention relates to a printer capable of device calibration.

2. Related Art

Inkjet printers that print on print media by ejecting ink from ink nozzles are common today. Because such printers are susceptible to printing defects such as blotchy colors due to conditions of the printer, detecting such problems and adjusting the printer accordingly is necessary.

In the case of a large format printer, this device calibration task is generally done when assembling the printhead or replacing the printhead during maintenance. This task involves visually checking the printed output of a test pattern, and based on the results, manually configuring settings related to the printing operation.

JP-A-2005-53228 describes related technology for calibrating a scanner in a configuration having a scanner disposed to a carriage together with the ink cartridges.

However, such conventional manual methods of device calibration are complicated, time consuming, and labor intensive.

Automating device calibration by photographing a test pattern with a camera is conceivable, but precise imaging is important to calibrate a device with high precision, and precise installation and positioning of the camera must therefore also be considered. The technology disclosed in JP-A-2005-53228 is silent regarding detecting errors in the installation position of the camera.

SUMMARY

At least one objective of the present invention is therefore to provide a printer that can improve the installation position of a camera for photographing a test pattern, and is capable of automatic, precise device calibration.

A printer according to one aspect of the invention has a carriage configured to support and move a printhead; a camera attached to the carriage and configured to photograph an image printed by the printhead; an adjustment mechanism configured to adjust an installation position of the camera; and a processor configured to control to move the carriage to a position of a predetermined specific mark, photograph the specific mark by the camera, and based on a photographed image of the specific mark, adjust an installation position of the camera by the adjustment mechanism.

This aspect of the invention improves the precision of the installation position of the camera, improves the precision of images photographed by the camera, and thereby improves the precision of device adjustment (calibration).

Preferably, the specific mark includes a center point mark; and the processor is configured to control to adjust a position of the camera in a plane parallel to the photographed surface based on an image of the center point mark photographed by the camera.

This aspect of the invention improves positioning precision of the camera in a plane parallel to the surface of the photographed image.

Preferably in another aspect of the invention, the specific mark includes a plurality of line markers disposed at a specific interval; and the processor is configured to control adjusting tilting of the camera based on an image of the plural line markers photographed by the camera.

This aspect of the invention assures the camera is set to the correct attitude.

Preferably in another aspect of the invention, the specific mark includes a rectangular mark; and the processor is configured to control to adjust an angle of view of the camera based on an image of the rectangular mark photographed by the camera.

This aspect of the invention enables appropriately adjusting the angle of view of the camera.

Preferably in another aspect of the invention, the specific mark includes a line mark; and the processor is configured to control to adjust a resolution of the camera based on a width of the line mark photographed by the camera.

This aspect of the invention enables appropriately adjusting the resolution of the camera.

Preferably in another aspect of the invention, the processor is configured to control the adjustment mechanism and adjust an installation position of the camera.

This aspect of the invention enables automatically adjusting the position of the camera, thereby eliminating the need for manual adjustment.

Another aspect of the invention is a control method of a printer having a carriage configured to carry and move a printhead, a camera attached to the carriage and configured to photograph an image printed by the printhead, and an adjustment mechanism configured to adjust an installation position of the camera, the control method including: moving the carriage to a position of a predetermined specific mark; photographing the specific mark by the camera; and based on a photographed image of the specific mark, adjusting an installation position of the camera by the adjustment mechanism.

Other objects and attainments together with a fuller understanding of the invention will become apparent and appreciated by referring to the following description and claims taken in conjunction with the accompanying drawings.

DESCRIPTION OF EMBODIMENTS

Figure 1:
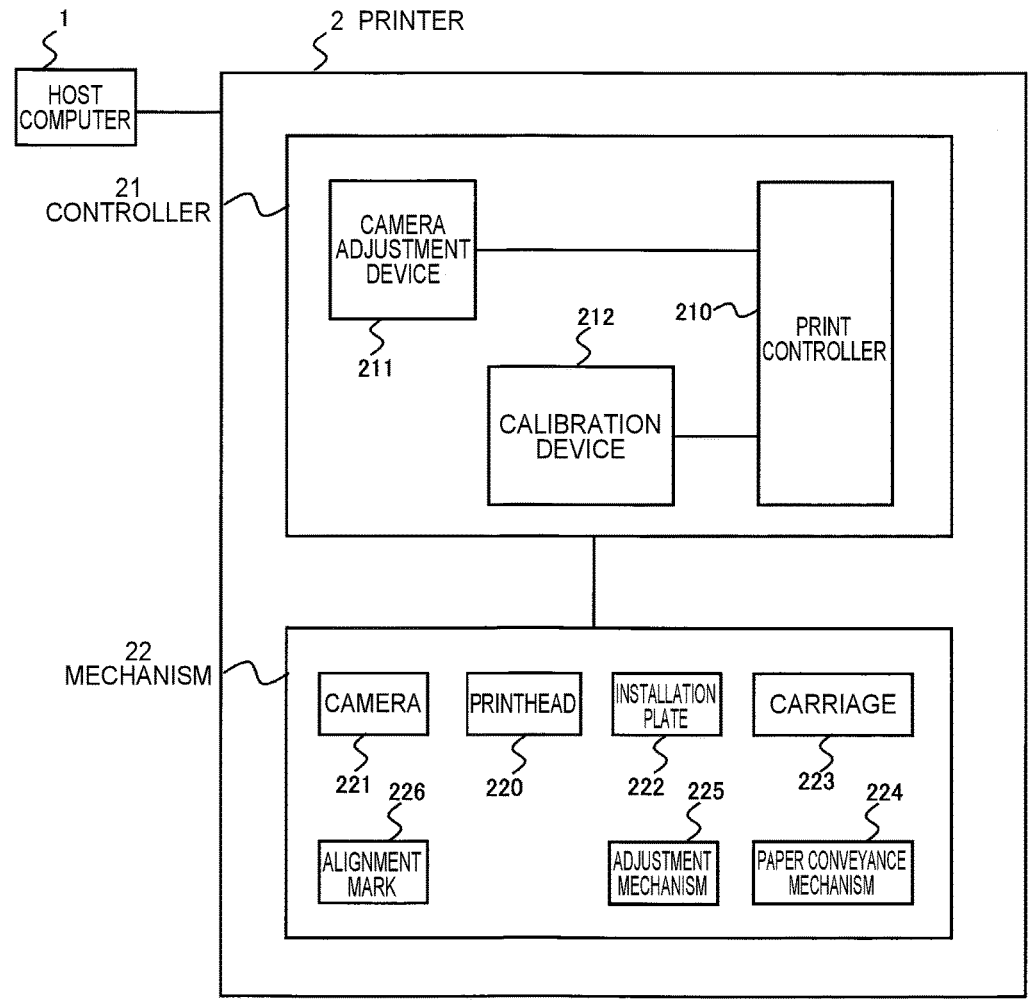
FIG. 1 schematically illustrates the configuration of a printer according to a preferred embodiment of the invention.

An embodiment of the present invention is described below with reference to the accompanying figures. However, the embodiment described below does not limit the technical scope of the invention. Note that in the figures like or similar parts are identified by the same reference numerals or reference symbols.

FIG. 1 schematically illustrates the configuration of a printer according to the invention. The printer 2 shown in FIG. 1 is a printer described as a preferred embodiment of the invention.

This printer 2 has a printhead 220 and a camera 221 mounted on a carriage 223, photographs a printed test pattern with the camera 221, and performs a device adjustment (calibration) process. When installing the camera 221, for example, the printer 2 images an alignment mark 226 disposed at a specific location with the camera 221, and based on the imaging result, adjusts the installation position of the camera 221. This process improves the installation precision of the camera 221, and enables precise, automatic device calibration.

As shown in FIG. 1, the printer 2 according to this embodiment of the invention is a printer configured to execute printing on paper M or other print medium in response to a print request from a host computer 1, for example, and in this example is a large format inkjet printer used to print advertisements and posters.

As shown in FIG. 1, the printer 2 includes a controller 21 and a mechanism 22.

The controller 21 is a controller that controls other parts of the printer 2, and is embodied by memory storing a program describing the content of a process, a CPU (processor) that executes processes according to the program, RAM, memory such as ROM that stores programs, or an ASIC device. The CPU, by reading and running a program stored in ROM, functions as a print controller 210, camera adjustment device 211, and calibration device 212.

The printer 2 has a normal mode (printing mode) and an inspection mode.

In the normal mode, when print data is received from the host computer 1, for example, the controller 21 controls the printhead 220, the carriage 223, and the paper conveyance mechanism 224 based on the print data, and executes the requested printing process on the paper M or other print medium. When controlling the printhead 220, the controller 21 causes the printhead 220 to eject (discharge) ink from multiple nozzles of the printhead 220.

In the inspection mode for device adjustment (calibration), the controller 21 controls the mechanism 22 described below to execute processes including printing a test pattern, imaging (photographing) the test pattern, image processing the resulting photograph (image data), analyzing the image data, and an adjustment process based on the results of analysis.

When the image data of the printed test pattern contains parts with dark colors or light colors, for example, the adjustment process increases or decreases the amount of ink ejected from the nozzles of the printhead 220 forming the dark color or light color to produce a uniform density. In addition, when deviation (error) is detected in the photographed image data, the ejection timing of the target nozzles is adjusted to eliminate the error. The adjustment values for the ink ejection volume and the ejection timing of the nozzles are stored in memory, and when printing, the controller 21 reads the values from memory to control the nozzles and eject ink.

The printer 2 also has a camera adjustment mode that is executed when a camera 221 is installed, for example. Note that the content of the process executed in the camera adjustment mode is described below.

The controller 21 has a functional configuration such as shown in FIG. 1. The controller 21 includes a print controller 210, a camera adjustment device 211, and a calibration device 212.

When a print request is sent to the printer 2, the print controller 210 interprets the print data, and based on the result controls parts of the mechanism 22 and executes the printing process on the print medium (such as paper M).

In the inspection mode, the print controller 210 prints a test pattern.

The camera adjustment device 211 starts operating in the camera adjustment mode, and controls the process of adjusting the installation position of the camera 221. While the specific content of this process is described further below, the camera adjustment device 211 images the alignment mark 226 with the camera 221, and based on the image data captured by the photograph, detects error in the installation position of the camera 221, and controls the adjustment mechanism 225 described below to set the installation plate 222 and camera 221 to the correct positions. When the camera 221 is adjusted to the correct position by the adjustment mechanism 225, the printhead 220 that is mounted on the installation plate 222 with the camera 221 is also set to the correct position.

The calibration device 212 controls processing in the inspection mode described above.

The mechanism 22 is controlled by the controller 21, and executes the printing process in the normal mode, and the imaging process in the inspection mode and camera adjustment mode. As shown in FIG. 1, the mechanism 22 includes a printhead 220, a camera 221, an installation plate 222, a carriage 223, a paper conveyance mechanism 224, an adjustment mechanism 225, and an alignment mark 226.

Figure 2:
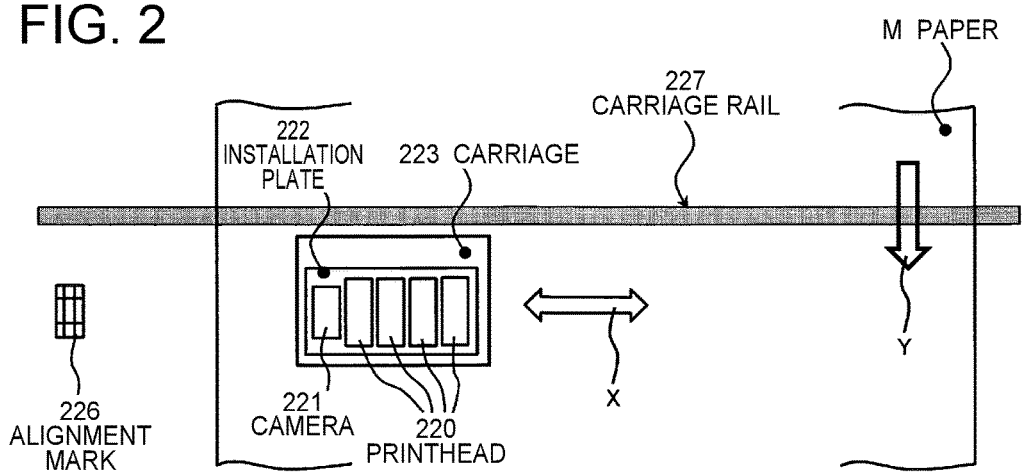
FIG. 2 is a plan view schematically illustrating the mechanism 22 around the carriage 223.

FIG. 2 is a plan view schematically illustrating the mechanism 22 around the carriage 223.

The printhead 220 has a plurality of nozzles, and ejects ink from the nozzles to the paper M, forming images on the paper M and printing according to commands from the controller 21 (print controller 210).

As shown in FIG. 2, a plurality of printheads 220 are provided and mounted on the carriage 223. In one example in which four colors of ink are used, there is a printhead 220 for each color of ink.

In the inspection mode, the camera 221 (imaging device) takes a picture of the paper M as the print medium and generates image data representing the image (test pattern) printed on the paper M, and in the camera adjustment mode, takes a picture of the alignment mark 226 and generates image data representing the alignment mark 226. As shown in FIG. 2, the camera 221 is carried on the carriage 223. In one example, the camera 221 includes a CMOS sensor or other type of imaging element, and a lens.

A light source is disposed near the camera 221, and the light source emits light enabling imaging by the camera 221. The light source emits light to the subject of the camera 221 (the imaged area), and light output is adjustable. The light source in this example comprises multiple LED lamps.

The installation plate 222 attaches the printhead 220 and camera 221 to the carriage 223, and in this example the installation plate 222 is therefore a metal plate. The printhead 220 and camera 221 are installed and fastened to the installation plate 222, and the installation plate 222 is attached to the carriage 223. The installation plate 222 can be moved and its position adjusted in multiple directions by the adjustment mechanism 225, and after adjustment, the position of the installation plate 222 on the carriage 223 is fixed.

The carriage 223 carries the printhead 220 and camera 221, and moves them in the scanning direction (indicated by the arrow X in FIG. 2). The carriage 223 drives along the carriage rail 227 by means of a motor or other drive source, and gears, a belt, or other power transfer mechanism. The carriage 223 moves as controlled by the print controller 210 when printing, for example.

As shown in FIG. 2, when printing, ink is ejected from the printhead 220 moving by means of the carriage 223 in the main scanning direction onto the paper M being conveyed in the sub-scanning direction (in the direction of arrow Y in FIG. 2), and an image is formed on the paper M.

The paper conveyance mechanism 224 is a device that conveys the paper M in the sub-scanning direction, and includes conveyance rollers, a drive source for the rollers, a power transfer mechanism, and a conveyance path. The paper conveyance mechanism 224 is driven as controlled by the print controller 210 when printing, for example.

Figure 3:
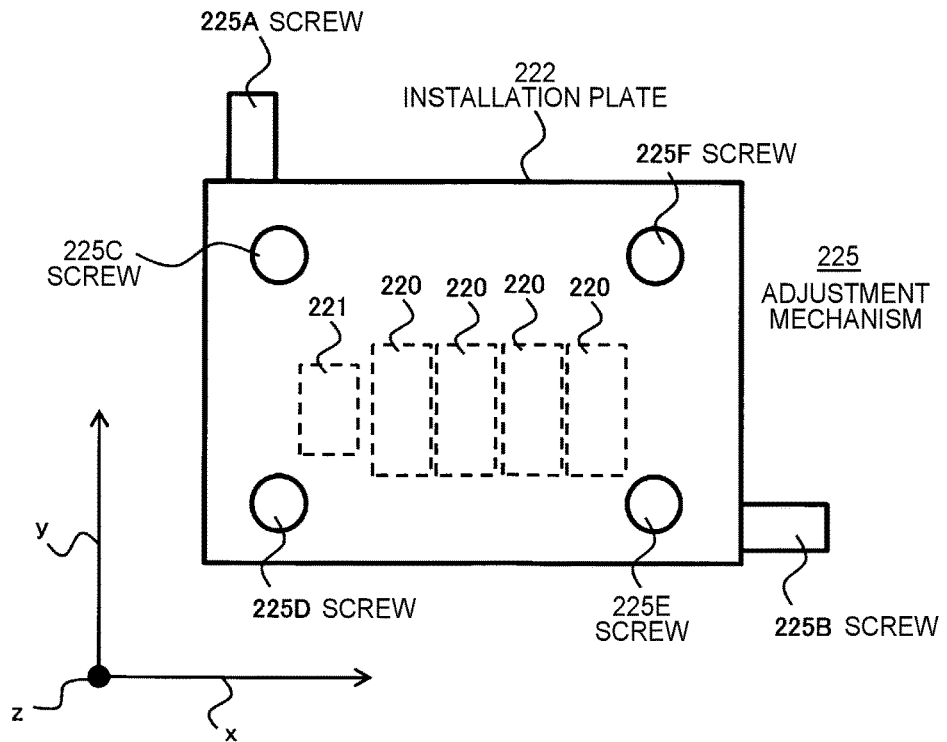
FIG. 3 is a plan view schematically illustrating the adjustment mechanism 225.

The adjustment mechanism 225 is a mechanism configured to adjust the position of the installation plate 222, that is, adjust the position of the camera 221 and printhead 220. FIG. 3 is a plan view schematically illustrating the adjustment mechanism 225. Six screws 225A to 225F of the adjustment mechanism 225 are shown in FIG. 3. Note that in FIG. 3 the X-axis is parallel to the main scanning direction of the carriage 223, the Y-axis is parallel to the sub-scanning direction, and the Z-axis is perpendicular to the X-axis and the Y-axis (perpendicular to the surface of the paper M).

A motor and position detector (encoder) are disposed to the screws 225A to 225F, and each of the screws 225A to 225F can turn independently as controlled by the camera adjustment device 211. When turned, screw 225A moves the installation plate 222 on the Y-axis. When turned, screw 225B moves the installation plate 222 on the X-axis. When turned, screws 225C to 225F move the installation plate 222 on the Z-axis. Note that because screws 225C to 225F move independently of each other, the installation plate 222 can be tilted in different directions relative to the Z-axis by adjusting the positions (rotation) of the screws 225C to 225F.

The alignment mark 226 (positioning mark) is a mark for adjusting the installation position of the camera 221 to the correct position, and is disposed to a specific position that can be imaged by the camera 221, such as the home position (standby position) of the carriage 223 (see FIG. 2). The home position is a position removed from the position where the paper M is located.

By disposing the alignment mark 226 to this position, by a single scan of the carriage 223, or without moving the paper M by the paper conveyance mechanism 224, any two or more of the processes of printing a test pattern on the paper M by the printhead 220, imaging the alignment mark 226 by the camera 221, and imaging the test pattern on the paper M by the camera 221, can be executed. The alignment mark 226 comprises various line markers printed so they can be read from a flat member (such as a structural member or a cover member) of the printer 2. These line markers are printed on a panel member in this example.

Figure 4:
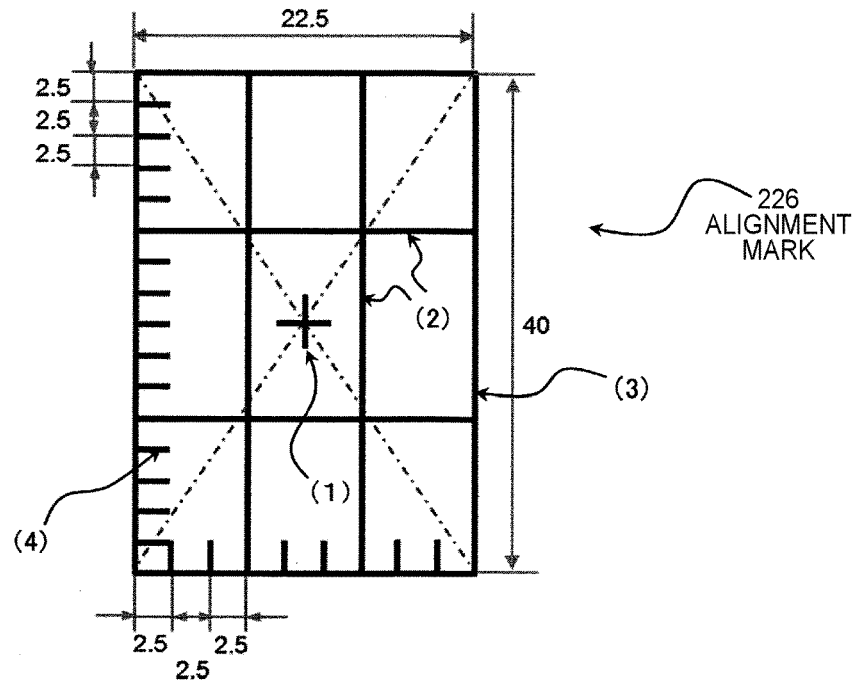
FIG. 4 shows an example of an alignment mark 226.

FIG. 4 shows an example of an alignment mark 226. The alignment mark 226 shown in FIG. 4 is a graphic visible on the Z-axis shown in FIG. 3, in other words, visible in the direction from the camera 221 to the surface of the paper M. The horizontal direction in FIG. 4 is the same as the X-axis in FIG. 3, and the vertical direction in FIG. 4 is the Y-axis in FIG. 3.

The alignment mark 226 shown in FIG. 4 includes four types of line markers ((1) to (4)). How these line markers are used is described further below. Note that the numbers shown in FIG. 4 are examples of dimensions, the unit of which is millimeters in this example. The size of the alignment mark 226 is smaller than the imaging area of the camera 221.

The printer 2 configured as described above according to this embodiment operates in a normal mode and an inspection mode. In the normal mode, the printer 2 receives print requests (print data) from the host computer 1, and in response, the controller 21 (print controller 210) controls parts of the mechanism 22 to print on the paper M, which is the print medium. More specifically, the printhead 220 moves in the main scanning direction, ejects ink onto the paper M conveyed in the sub-scanning direction, and forms images. After printing, the paper M is discharged by the paper conveyance mechanism 224.

In the inspection mode, to check the printing condition of the printer 2, processes including printing a test pattern, imaging the test pattern, detecting printing defects based print medium the image data, and making adjustments to resolve the printing defects, are executed as controlled by the calibration device 212.

The printer 2 according to this embodiment of the invention is characterized by the process of adjusting the position of the camera 221 in the camera adjustment mode as described more fully below.

Figure 5:
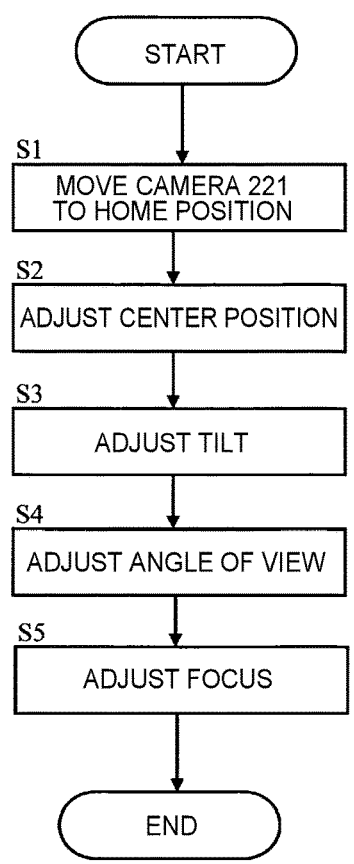
FIG. 5 is a flow chart showing steps in the process executed in the camera adjustment mode.

FIG. 5 is a flow chart showing an example of steps in the process executed in the camera adjustment mode. Note that the camera adjustment mode starts when a camera 221 is installed (during printer 2 assembly, or when the camera 221 is replaced, for example).

The camera adjustment mode is started by a specific user operation of a button, switch, keyboard, mouse, or other operating member of the printer 2 or host computer 1, or automatically when the camera 221 is installed.

First, the camera adjustment device 211 starts and controls the carriage 223 to move the camera 221 to the position of the alignment mark 226 (step S1 in FIG. 5). More specifically, the camera adjustment device 211 moves the camera 221 in the scanning direction to the specific position (such as the home position) where the alignment mark 226 is located so that the camera 221 is positioned opposite the alignment mark 226 on the Z-axis in FIG. 3, that is, is positioned where the camera 221 can photograph the alignment mark 226.

The camera adjustment device 211 then photographs the alignment mark 226, detects error, and adjusts the position of the camera 221 for the following four items.

Figure 6:
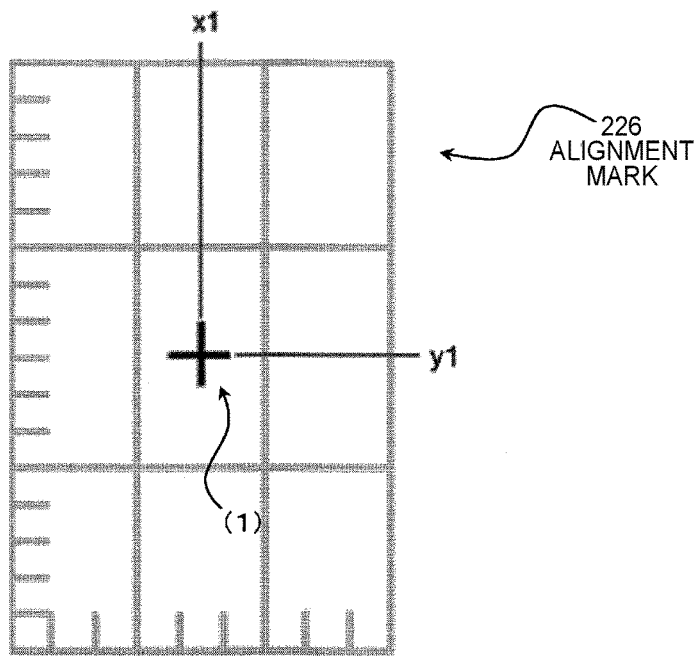
FIG. 6 describes adjusting the center point.

First, the camera adjustment device 211 executes a process to adjust the center position of the camera 221 (step S2 in FIG. 5). This adjustment of the center position adjusts the position of the camera 221 on the X-axis and Y-axis in FIG. 3 (adjusts the position in a plane parallel to the image surface). FIG. 6 describes this center position adjustment. In FIG. 6 and FIG. 7 to FIG. 9 described below, the (line markers of the) alignment mark 226 are shown in the same directions as in FIG. 4. Therefore, the horizontal axis in these figures is the X-axis in FIG. 3, and the longitudinal (top-bottom) axis in the figures is the Y-axis in FIG. 3. The coordinates xi and yi in the figures indicate the distance on the X-axis and the Y-axis, respectively, from a single specific origin in the rectangle forming the imaging area of the camera 221.

The center position adjustment uses line markers (1) (center point mark) in the alignment mark 226. The camera adjustment device 211 images the alignment mark 226 with the camera 221, analyzes the captured image data, and obtains the values (actual values) of coordinate x1 and coordinate y1 at the intersection of the line markers (1) as shown in FIG. 6.

The camera adjustment device 211 then compares the predetermined reference values of coordinate x1 and coordinate y1 with the actual values, and if there is no difference therebetween, determines the camera 221 is at the correct position on the X-axis and the Y-axis, and ends the process adjusting the center position.

If there is a difference between the reference values and actual values, the camera adjustment device 211 moves the camera 221 a distance appropriate to the difference by means of the adjustment mechanism 225. This adjustment of the center position is done by driving either or both screw 225A and screw 225B. As a result, the camera 221 is set to the correct position on the X-axis and Y-axis.

Figure 7:
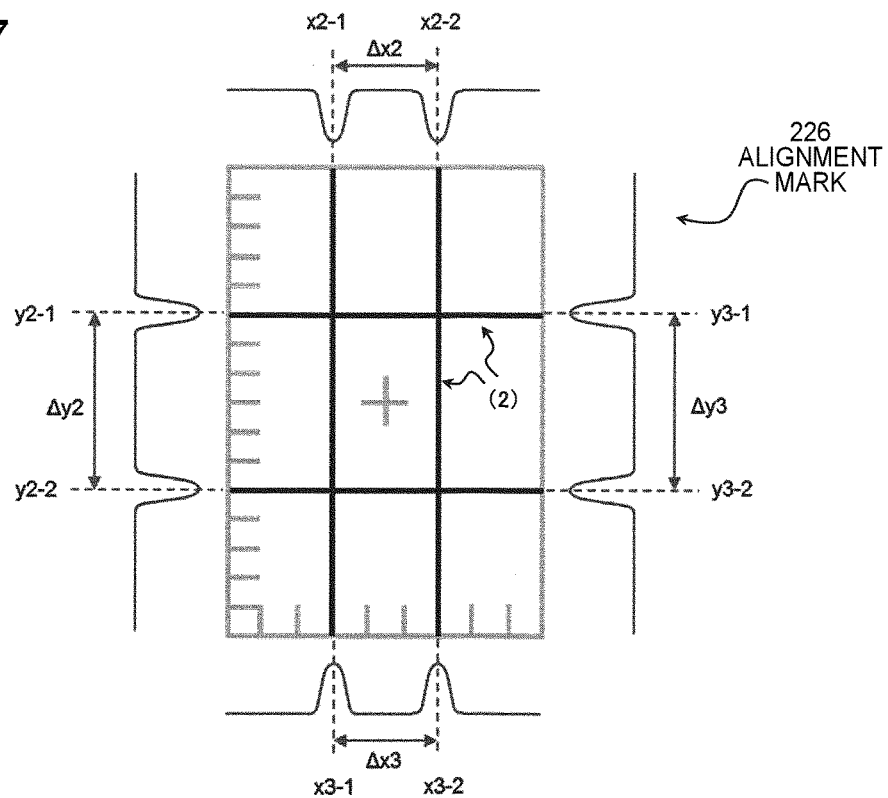
FIG. 7 describes skew adjustment.

Next, the camera adjustment device 211 executes an adjustment process for skewing (tilting) of the camera 221 (step S3 in FIG. 5). This adjustment of skewing is an adjustment of inclination of the imaging direction of the camera 221 to the Z-axis shown in FIG. 3 (that is, expressed in terms of tilting the position of a person's head, shaking the head sideways (tilting on the X-axis), nodding up and down (tilting on the Y-axis), and tilting other than sideways and up/down (tilting on the X-axis and Y-axis). FIG. 7 describes skewing (tilt) adjustment.

The line markers (2) of the alignment mark 226 (a plurality of line markers disposed at a specific interval) are used for tilt adjustment. The camera adjustment device 211 photographs the alignment mark 226 by the camera 221, analyzes the image data acquired from the photograph, and as shown in FIG. 7, calculates the values (actual values) of the coordinates x2-1, x2-2, x3-1, x3-2, y2-1, y2-2, y3-1, y3-2 at specific parts of the line markers (2).

Next, the camera adjustment device 211 checks for nodding (tilting on the Y-axis). More specifically, the camera adjustment device 211 calculates $\Delta x2=(x2\text{-}1)-(x2\text{-}2)$ and $\Delta x3=(x3\text{-}1)-(x3\text{-}2)$, and if $\Delta x2=\Delta x3$, determines there is no nodding.

Next, the camera adjustment device 211 checks for sideways tilt. More specifically, the camera adjustment device 211 calculates $\Delta y2=(y2\text{-}1)-(y2\text{-}2)$ and $\Delta y3=(y3\text{-}1)-(y3\text{-}2)$, and if $\Delta y2=\Delta y3$, determines there is no sideways tilt (tilting on the X-axis).

Next, the camera adjustment device 211 checks for skewing. More specifically, the camera adjustment device 211 calculates $\Delta x21=(x2\text{-}1)-(x3\text{-}1)$, $\Delta x32=(x2\text{-}2)-(x3\text{-}2)$, $\Delta y21=(y2\text{-}1)-(y3\text{-}1)$, and $\Delta y32=(y2\text{-}2)-(y3\text{-}2)$, and if $\Delta x21=\Delta x32=\Delta y21=\Delta y32=0$, determines there is no skewing.

As a result of the above checks, if the camera adjustment device 211 determines there is no nodding, sideways tilt, or skewing, the camera adjustment device 211 determines the camera 221 is positioned correctly with respect to these parameters, and ends the skewing (tilt) adjustment process.

However, if the camera adjustment device 211 determines there is any nodding, sideways tilt, or skewing, the camera adjustment device 211 moves the camera 221 an amount appropriate to the error (tilt) by means of the adjustment mechanism 225. Screw 225C to screw 225F are driven to adjust any tilt. As a result, tilting of the camera 221 is eliminated, and the camera 221 is set to the correct attitude.

Figure 8:
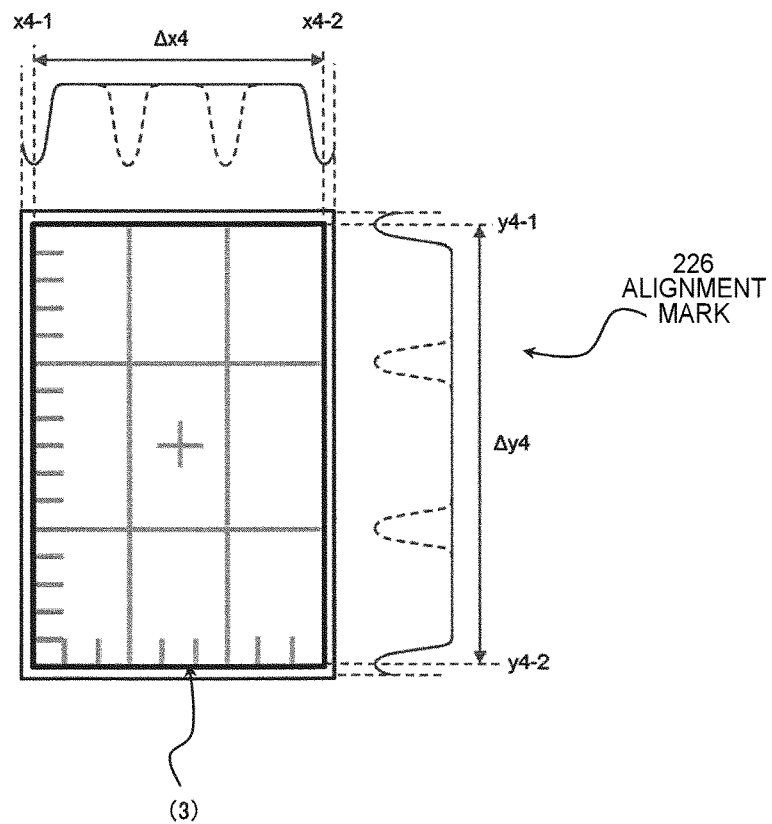
FIG. 8 describes the angle of view.

Next, the camera adjustment device 211 adjusts the angle of view of the camera 221 (step S4 in FIG. 5). Adjusting the angle of view is adjustment of the position on the Z-axis in FIG. 3. FIG. 8 describes adjusting the angle of view.

The line markers (3) of the alignment mark 226 (rectangular markers) are used for angle of view adjustment. The camera adjustment device 211 photographs the alignment mark 226 by the camera 221, analyzes the image data acquired from the photograph, and as shown in FIG. 8, calculates the values (actual values) of the coordinates x4-1, x4-2, y4-1, and y4-2 of the four corners of the rectangular line markers (3).

Next, the camera adjustment device 211 calculates the values (actual values) $\Delta x4=(x4\text{-}1)-(x4\text{-}2)$ and $\Delta y4=(y4\text{-}1)-(y4\text{-}2)$, and compares the results with predetermined reference values for $\Delta x4$ and $\Delta y4$.

If there is no difference, the camera adjustment device 211 determines the camera 221 is positioned correctly on the Z-axis, and ends the angle of view adjustment.

However, if there is a difference between the reference value and actual value, the camera adjustment device 211 moves the camera 221 a distance appropriate to the difference by means of the adjustment mechanism 225. Screw 225C to screw 225F are driven to adjust for any tilt. As a result, the camera 221 is set to the correct position on the Z-axis.

Figure 9:
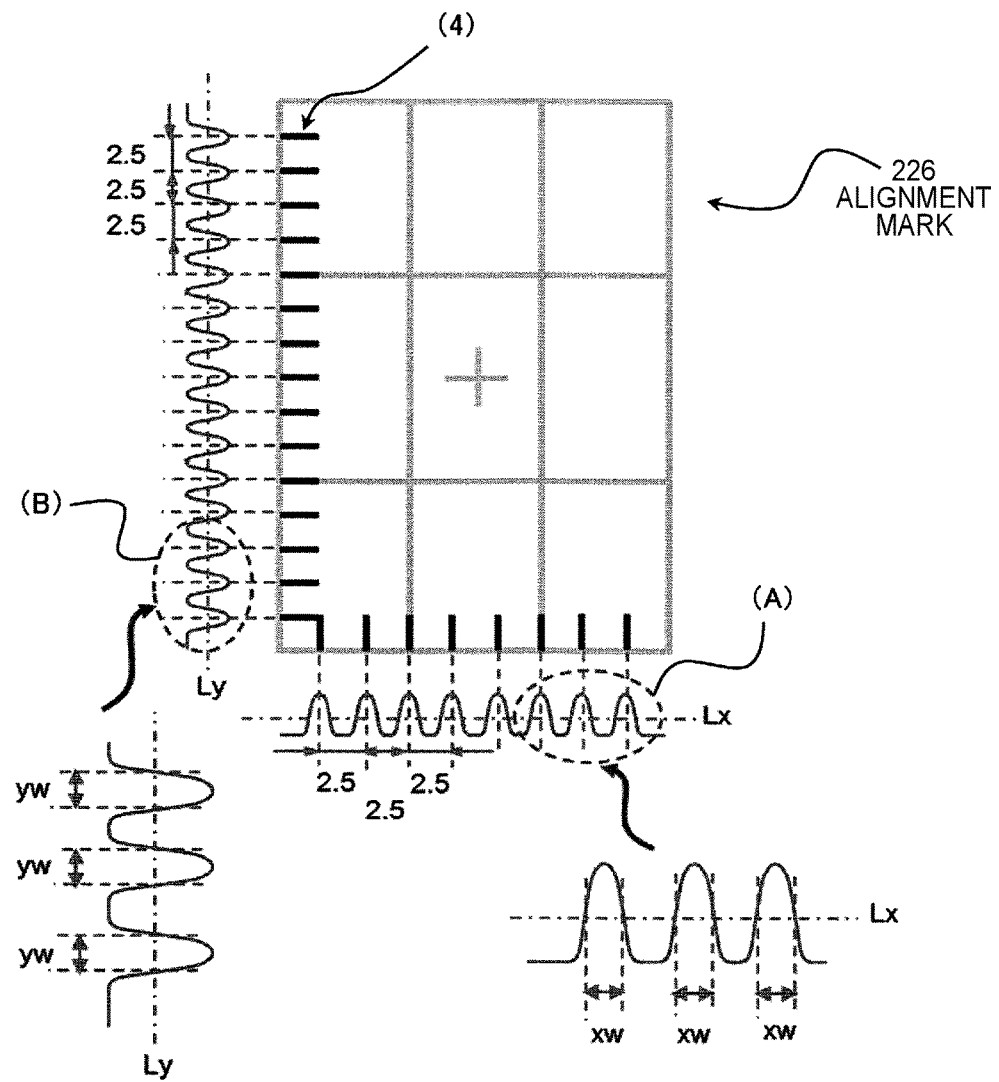
FIG. 9 describes focus adjustment.

Next, the camera adjustment device 211 adjusts the focus of the camera 221 (step S5 in FIG. 5). Focus adjustment is adjustment of the position on the Z-axis in FIG. 3. FIG. 9 describes adjusting the focus. Note that focus adjustment may also referred to as adjustment of the resolution.

The line markers (4) of the alignment mark 226 are used to adjust the focus. The camera adjustment device 211 photographs the alignment mark 226 by the camera 221, analyzes the image data acquired from the photograph, and as shown in FIG. 9, calculates the value (actual value) of the width xw of the vertical lines and the width yw of the horizontal lines of the rectangular line markers (4). More specifically, the camera adjustment device 211, as indicated by the enlarged views of the areas inside ovals (A) and (B) in FIG. 9, acquires as width xw and width yw the width across lines Lx and Ly at predetermined positions through the density gradation waves represented by the sine waves in FIG. 9.

Next, the camera adjustment device 211 then compares the values (actual values) of width xw and width yw thus acquired with predetermined reference values (min) of the widths, and if there is no difference therebetween, determines the camera 221 is positioned correctly on the Z-axis, and ends the focus adjustment.

If there is a difference between the reference values and the actual values, the camera adjustment device 211 moves the camera 221 a distance appropriate to the difference by means of the adjustment mechanism 225. Screw 225C to screw 225F are driven to adjust the focus. As a result, the camera 221 is set to the correct position on the Z-axis.

The installation position of the camera 221 is adjusted by the camera adjustment device 211 as described above.

Note that adjusting only one of the angle of view and the focus is also conceivable.

In the four adjustment processes described above, the camera may be driven to take a picture again after moving the camera 221 by the adjustment mechanism 225 to confirm the adjustment. If the result determines that the camera 221 is not in the correct position and attitude, the camera 221 may be moved again by the adjustment mechanism 225.

Furthermore, in the embodiment described above, the installation plate 222 is moved automatically by the adjustment mechanism 225, but the amount the screws 225A to 225F must be turned for adjustment (movement) may be displayed on the display device of the printer 2 for the user, and the user prompted to manually turn the screws 225A to 225F as required.

Note also that the camera adjustment device 211 may be disposed to another device (such as the host computer 1) that can communicate with the printer 2.

As described above, a printer 2 according to this embodiment of the invention has a camera 221 on a carriage 223, and images a printed test pattern with the camera 221 for device calibration, but the installation position of the camera 221 is adjusted by the camera adjustment device 211 when the camera 221 is installed, for example. The accuracy of the image data captured by photographing with the camera 221 is therefore increased, and the device can be calibrated with great precision. As a result, high quality printing is possible.

Furthermore, because camera adjustment and calibration are done automatically, manual intervention and operator time are not required. In addition, because the precision of the installation position of the camera 221 is improved, a larger effective imaging area can be achieved, calibration can be completed efficiently, and calibration precision can be improved because the size of the test pattern can be increased.

Furthermore, the alignment mark 226 includes various types of line markers, and these line markers can be used to finely adjust the position and attitude (tilt) of the camera 221 in three dimensions, thereby enabling high precision imaging.

Note that the invention can be applied to printers that print by printing methods other than inkjet.

The invention being thus described, it will be obvious that it may be varied in many ways. Such variations are not to be regarded as a departure from the spirit and scope of the invention, and all such modifications as would be obvious to one skilled in the art are intended to be included within the scope of the following claims.

What is claimed is:

1. A printer comprising:
   a carriage configured to support and move a printhead;
   a camera attached to the carriage and configured to photograph an image printed by the printhead;
   an adjustment mechanism configured to adjust an installation position of the camera; and
   a processor configured to control to move the carriage to a position of a predetermined specific mark, photograph the specific mark by the camera, and based on a photographed image of the specific mark, adjust an installation position of the camera by the adjustment mechanism,
   wherein the processor is further configured to control the adjustment mechanism and adjust an installation position of the camera.

2. The printer described in claim 1, wherein:
   the specific mark includes a center point mark; and
   the processor is configured to control to adjust a position of the camera in a plane parallel to the photographed surface based on an image of the center point mark photographed by the camera.

3. The printer described in claim 1, wherein:
   the specific mark includes a plurality of line markers disposed at a specific interval; and
   the processor is configured to control adjusting tilting of the camera based on an image of the plural line markers photographed by the camera.

4. The camera described in claim 1, wherein:
   the specific mark includes a rectangular mark; and
   the processor is configured to control to adjust an angle of view of the camera based on an image of the rectangular mark photographed by the camera.

5. The camera described in claim 1, wherein:
   the specific mark includes a line mark; and
   the processor is configured to control to adjust a resolution of the camera based on a width of the line mark photographed by the camera.

6. A control method of a printer having a carriage configured to support and move a printhead, a camera attached to the carriage and configured to photograph an image printed by the printhead, and an adjustment mechanism configured to adjust an installation position of the camera, the control method comprising:
   moving the carriage to a position of a predetermined specific mark;
   photographing the specific mark by the camera;
   based on a photographed image of the specific mark, adjusting an installation position of the camera by the adjustment mechanism; and
   controlling the adjustment mechanism and adjusting an installation position of the camera.

7. The control method of a printer described in claim 6, wherein:
   the specific mark includes a center point mark;
   the control method including adjusting a position of the camera in a plane parallel to the photographed surface based on an image of the center point mark photographed by the camera.

8. The control method of a printer described in claim 6, wherein:
   the specific mark includes a plurality of line markers disposed at a specific interval;
   the control method including adjusting tilting of the camera based on an image of the plural line markers photographed by the camera.

9. The control method of a printer described in claim 6, wherein:
   the specific mark includes a rectangular mark;
   the control method including adjusting an angle of view of the camera based on an image of the rectangular mark photographed by the camera.

10. The control method of a printer described in claim 6, wherein:
    the specific mark includes a line mark;
    the control method including adjusting a resolution of the camera based on a width of the line mark photographed by the camera.

* * * * *